United States Patent [19]

Strom

[11] 4,354,047

[45] Oct. 12, 1982

[54] NICKEL CATALYSTS FOR OXIDATIVE COUPLING OF PHENOLS

[75] Inventor: Robert M. Strom, Midland, Mich.

[73] Assignee: The Dow Chemical Company, Midland, Mich.

[21] Appl. No.: 266,556

[22] Filed: May 22, 1981

[51] Int. Cl.$^3$ ............................................. C07C 39/14
[52] U.S. Cl. .................................... 568/730; 568/719; 568/723; 568/726; 260/396 N
[58] Field of Search ............... 568/730, 723, 719, 729, 568/726; 260/396 N

[56] References Cited

U.S. PATENT DOCUMENTS

| | | | |
|---|---|---|---|
| 4,096,190 | 7/1978 | Rutledge | 568/730 |
| 4,098,830 | 7/1978 | Rutledge | 568/730 |
| 4,100,205 | 7/1978 | Rutledge | 568/730 |
| 4,101,561 | 7/1978 | Rutledge | 568/730 |
| 4,108,908 | 8/1978 | Rutledge | 568/730 |
| 4,132,722 | 1/1979 | Rutledge | 568/730 |
| 4,139,544 | 2/1979 | Rutledge | 568/730 |
| 4,156,788 | 5/1979 | Earley | 568/730 |
| 4,195,189 | 3/1980 | Rutledge | 568/730 |

OTHER PUBLICATIONS

"The Encyclopedia of Chemistry" 3rd Ed. Reinhold (1973) New York, pp. 209–213.
Plummer "Bertchte" vol. 59, pp. 2159–2175 (1926).
Clemo et al. "J. Chem. Soc." (1931), pp. 1265–1273.

*Primary Examiner*—Werren B. Lone
*Attorney, Agent, or Firm*—Douglas N. Deline

[57] ABSTRACT

Carbon-to-carbon coupled self-condensation products are obtained by the oxidative coupling of substituted phenols in the presence of a heterogeneous dehydrogenation catalyst comprising nickel.

12 Claims, No Drawings

NICKEL CATALYSTS FOR OXIDATIVE COUPLING OF PHENOLS

BACKGROUND OF THE INVENTION

The invention relates to an improved method of producing binary self condensation products of phenols. It is well-known in the art that substituted phenols can be oxidized to yield self-condensation products, especially diphenoquinones and biphenols. The diphenoquinones are useful antioxidants. Biphenols are useful antioxidants, stabilizers and intermediates for the synthesis of various polymers, especially polyesters.

In U.S. Pat. No. 4,195,189, a one-step process for the oxidative coupling of phenols is described wherein molten phenols are combined with an oxidizing agent which is activated copper oxide. The copper oxide was employed in about equal or greater molar ratio with the phenolic compound. In this process the copper oxide is employed not as a catalyst but as a source of oxygen as no oxygen or oxygen-containing gas is otherwise present during the reaction.

In German Pat. No. 536,277, the oxides of copper, manganese and lead were employed in the oxidative reaction of phenol. The reaction product, however, was most probably a polymeric material as it was described as a light grey amorphous precipitate without a sharp melting point which sintered to a brown mass at 120° C. to 130° C. Diphenoquinone is a highly colored crystalline material which melts at about 165° C.

SUMMARY OF THE INVENTION

The present invention comprises an improved process for the carbon-carbon oxidative coupling of phenols. Accordingly, diphenoquinones and biphenols are prepared by carbon-carbon coupling in accordance with the following general reactions depending on the reactive sites available in the phenol employed.

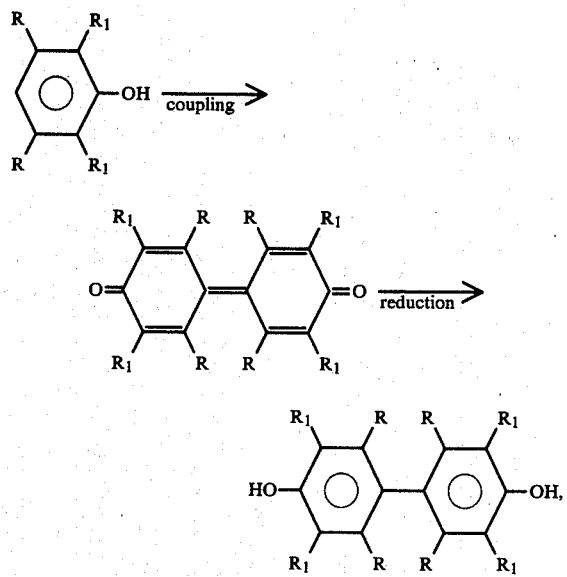

Each R is either hydrogen, halogen or $R_1$, and each $R_1$ is a substituent having up to 10 carbons selected from hydrocarbon, halohydrocarbon or hydrocarbonoxy. Preferred phenol reactants are 2,6-disubstituted phenols which couple to form 3,3',5,5'-tetrasubstituted-p,p'-diphenoquinones. Most preferred are 2,6-dialkyl-substituted phenols. The phenol reactants are contacted in the presence of oxygen or an oxygen-containing gas with a heterogeneous dehydrogenation catalyst comprising nickel. The reaction is preferably conducted at elevated temperatures and pressures. The diphenoquinone reaction products were produced may be reduced by known methods, for example, by contact with a heterogeneous hydrogenation catalyst to produce the corresponding biphenol if desired. Also, if desired, where R is hydrogen and each $R_1$ is an alkyl group that is easily removable, the substituted biphenol may be dealkylated according to the invention to produce an unsubstituted biphenol. Suitable easily removable alkyl groups include tertiary butyl or tertiary amyl.

DETAILED DESCRIPTION OF THE INVENTION

The substituted phenol reactants here used are those well-known in the art as forming oxidative carbon-to-carbon coupling products. Examples are 2,6-dimethyl phenol, 2,6-diethyl phenol, 2,6-ditertiary butyl phenol, 2,6-diisobutyl phenol, 2-octyl-6-methyl phenol, 2,6-ditertiary-hexyl phenol, 2-ethyl-6-methyl phenol, 2-methyl-6-tertiary butyl phenol, 2-cyclohexyl-6-methyl phenol, 2,6-dimethoxy phenol, 2,6-dibutoxy phenol, 2-methoxy-3-ethoxy-6-methyl phenol, 2,4-dimethyl phenol, 2,4-ditertiary butyl phenol, 2-methyl-4-amyl phenol, 2-methyl-4-ethoxy phenol, 2-ethoxy-3,4-dimethyl phenol, 2,4-dimethyl-3,5-dichlorophenol, etc. Because of steric hinderance, when the 2,4-substituted phenolic compounds are coupled in the ortho position, the substituent on the 3-position is preferably hydrogen, halogen or a short-chain alkyl group. Generally like phenol compounds are coupled to reduce the variety of reaction products formed, unless of course a mixture of products is acceptable. As previously mentioned, the preferred phenolic reactant is 2,6-ditertiary butyl phenol.

The oxygen used is either oxygen itself or an oxygen-containing gas such as air. While any suitable pressure from atmospheric to elevated pressures may be employed, it is preferred, in order to produce improved reaction rates and yields, to employ elevated pressures. The reaction is normally conducted in a pressurized system with the oxygen-containing gas supplying the pressurizing means. Elevated pressures of up to about 500 psig may be employed depending on the amount of oxygen present in the gas mixture and the pressure vessel design limits. Utilizing air as the oxidizing medium pressures of about 100–450 psig are suitable.

The reaction is conducted at elevated temperatures of from about 30° C. to about 200° C., preferably from about 50° C. to about 150° C. and most preferably from about 60° C. to about 100° C. for the time necessary to form substantial amounts of the desired tetra-substituted diphenoquinone.

The process may be operated without a solvent, interchangeably referred to herein as a liquid reaction medium, in which case the substituted phenol itself acts as a solvent. However, preferably a liquid reaction medium is employed in order to aid in transport of reactants and in recovery of the products. Any liquid under the reaction conditions that is relatively unreactive is acceptable. The reactants and products need not be highly soluble therein and indeed may be insoluble. Examples include such organic liquids as lower carboxylic acids, alcohols, and aromatic compounds. Preferred solvents may differ depending on the nature of the phenol reactant, the catalyst and the reaction conditions employed. Particularly, preferred liquids are polar compounds, particularly lower alcohols which are not themselves easily oxidizable. An example is methanol.

The catalysts employed are heterogeneous dehydrogenation catalysts comprising nickel as the active catalytic species. The catalysts are well-known and may be purchased commercially. Generally, nickel-containing catalysts are provided as surface coatings of nickel oxide on an inert substrate such as carbon, silica, alumina, diatomaceous earth, clays, etc. Such substrates are employed to provide increased surface area for the catalyst. The nickel oxide may be present in amounts from about 1 percent up to about 70 percent or higher.

In the operation of the invention, the heterogeneous dehydrogenation catalyst is placed into a suitably designed reactor vessel fitted with a reactant inlet and product outlet along with heating means as well as an entrance and exit means for the oxygen-containing gas. Initially, the catalyst may be added in either a reduced or a highly oxidized state inasmuch as under the instant process conditions, the catalyst acquires the correct oxidation state to result in formation of carbon-carbon oxidatively coupled reaction products.

The reactor vessel is next charged with a solution of a substituted phenol in the previously described liquid reaction medium. In a batch operation, the reactor is then sealed and heated to the desired reaction temperatures accompanied by oxygen addition. Agitation, as for example by stirring, may also be employed. In a continuous operation, the reactant charge is supplied to a reactor containing the catalyst that is maintained at the desired temperature. A stream of oxygen-containing gas is also suppled to the reactor either concurrently or countercurrently and the product mixture is continuously removed.

The substituted diphenoquinone in the product mixture is separated from unreacted substituted phenol if necessary and may even be separated from the liquid reaction medium as by distillation or precipitation. Preferably, however, the crude mixture containing substituted diphenoquinone is further charged to a second reactor containing a heterogeneous hydrogenation catalyst maintained under reducing conditions. Suitable hydrogenation catalysts are those heterogeneous hydrogenation catalysts previously known in the art, such as the noble metals, nickel, copper chromite, etc. The reaction conditions employed are substantially modified from the oxidative coupling conditions initially employed in order to effect the desired hydrogenation. Generally, the hydrogenation is conducted at temperatures from about 25° C. to about 150° C. and pressures from about atmospheric to about 100 psig in the presence of a hydrogen-containing gas.

Alternatively, the reduction may be accomplished by reacting the diphenoquinone with additional phenol, or unreacted phenol from the oxidative coupling reaction in the presence of base at an elevated temperature as is previously known in the art and taught, for example, in U.S. Pat. No. 3,562,338 which teaching is incorporated herein by reference.

The hydrogenation product is the corresponding substituted biphenol which may be recovered from the reaction mixture. As previously mentioned, in a preferred phenol reactant, each $R_1$ is an alkyl group which may be removed by a suitable dealkylation process. Removal of such alkyl groups from the biphenol product, if desired, is accomplished according to well-known techniques. One suitable method is to heat the substituted biphenol at an elevated temperature below the decomposition temperature of the biphenol. This process is described and taught in U.S. Pat. No. 4,205,187 which teaching is incorporated herein by reference. Another process particularly effective when the alkyl groups are tertiary butyl or tertiary amyl, is to heat the alkylated biphenol in the presence of a catalytic amount of a strong acid such as p-toluene sulfonic acid. The alkyl group is effectively removed to yield the respective alkene, e.g., isobutene in the case of tertiary butyl groups, pentenes when tertiary amyl groups are employed, and the desired dealkylated biphenol product.

The isobutene or similar alkene so obtained may be recycled if desired to alkylate phenol itself resulting in production of the substituted phenols originally employed in the instant oxidative coupling step. The alkylation of phenols in this manner is well-known technology. Suitably, the phenol may be readily selectively alkylated by forming first the aluminum phenoxide which is then reacted by contacting with isobutene at elevated pressure and temperature. This process is well-known having been previously described in U.S. Pat. No. 2,831,898 which teaching is herein incorporated by reference.

The instant process allows for a large degree of flexibility in operation. The catalyst may be packed into a fixed bed inside a pressure reactor. It is further possible in a continuous process to employ several reactors, one for the oxidative coupling step and the other for the hydrogenation. The substituted phenol is reacted in the presence of oxygen to form diphenoquinone in the first reactor and subsequently the reaction mixture is charged to the second reactor where it is reduced preferably by the action of hydrogen.

SPECIFIC EMBODIMENT

Having described my invention, the following examples are provided as illustrative of the invention and are not to be construed as limiting.

Example 1

In a 600-ml Parr reactor equipped with a mechanical stirrer, temperature control and gas inlet was charged 2,6-di-t-butylphenol (25 g) and 50 ml of o-dichlorobenzene. A nickel catalyst, Harshaw Ni-0104 containing 60 percent nickel on Kieselguhr with a ratio of reduced nickel to total nickel of 0.60 (2.5 g) was added along with a small amount (0.5 g) of sodium carbonate to prevent isomerization of the reactant.

The reactor and contents were pressurized with oxygen gas to 250 psi and heated to 160° C. for 2 hours. Afterwards the reactor was vented and the contents removed for analysis by gas-liquid chromatography according to accepted techniques of chemical analysis. The desired product 3,3',5,5'-tetra-t-butyldiphenoquinone was present in 41 percent yield. Unreacted 2,6-di-t-butylphenol comprised 29 percent of the reaction mixture.

What is claimed is:

1. A process for preparing by an oxidation coupling reaction a carbon-carbon coupled condensation product of a substituted phenol of the formula

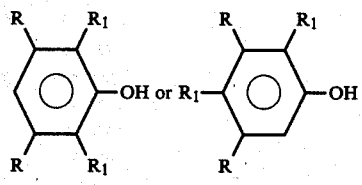

wherein each R is hydrogen, halogen or $R_1$, and each $R_1$ is a substituent having up to 10 carbons selected from the group consisting of hydrocarbon, halohydrocarbon and hydrocarbonoxy comprising contacting the substituted phenol with an oxygen-containing gas in the presence of a heterogeneous dehydrogenation catalyst comprising nickel in an oxidation state suitable for forming carbon-carbon oxidatively coupled reaction products.

2. A process according to claim 1 wherein the substituted phenol is a 2,6-dialkyl phenol.

3. A process according to claim 2 wherein the substituted phenol is 2,6-ditertiary butyl phenol.

4. A process according to claim 1 wherein the catalyst comprises an oxide of nickel.

5. A process according to claim 3 wherein the catalyst is supported by an inert supportive means.

6. A process according to claim 4 wherein the inert support means is alumina, carbon, silica, diatomaceous earth or clay.

7. A process according to claim 1 wherein an inert liquid reaction medium is also present.

8. A process according to claim 7 wherein the inert liquid reaction medium is a polar compound.

9. A process according to claim 8 wherein the inert liquid reaction medium is methanol.

10. A process according to claim 1 which is conducted at a temperature from about 30° C. to about 200° C. and at an elevated pressure of up to about 500 psig.

11. The process according to claim 1 wherein the substituted diphenoquinone is thereafter reduced.

12. The process according to claim 11 wherein the reduction is accomplished by contacting the substituted diphenoquinone with hydrogen-containing gas in the presence of a heterogeneous hydrogenation catalyst at a temperature from about 25° C. to about 150° C. and pressures from about atmospheric to about 100 psig.

* * * * *